(12) United States Patent
Laurent et al.

(10) Patent No.: US 7,801,333 B2
(45) Date of Patent: Sep. 21, 2010

(54) VISION SYSTEM AND A METHOD FOR SCANNING A TRAVELING SURFACE TO DETECT SURFACE DEFECTS THEREOF

(75) Inventors: John Laurent, Saint-Augustin-de-Desmaures (CA); Michel Doucet, Saint-Augustin-de-Desmaures (CA)

(73) Assignee: Institut National d'Optique, Sainte-Foy, Quebec (CA)

( * ) Notice: Subject to any disclaimer, the term of this patent is extended or adjusted under 35 U.S.C. 154(b) by 1392 days.

(21) Appl. No.: 11/143,227

(22) Filed: Jun. 2, 2005

(65) Prior Publication Data

US 2006/0274930 A1    Dec. 7, 2006

(51) Int. Cl.
 G06K 9/00       (2006.01)
 G06K 9/36       (2006.01)
 E01C 23/00      (2006.01)
 G01M 17/02      (2006.01)

(52) U.S. Cl. ............... 382/108; 382/104; 382/113; 382/181; 382/291; 73/146

(58) Field of Classification Search .......... 382/141, 382/321; 73/146
See application file for complete search history.

(56) References Cited

U.S. PATENT DOCUMENTS

| | | | | |
|---|---|---|---|---|
| 4,653,316 A | * | 3/1987 | Fukuhara | 73/146 |
| 4,796,998 A | * | 1/1989 | Soma et al. | 356/608 |
| 4,899,296 A | * | 2/1990 | Khattak | 702/40 |
| 5,163,319 A | * | 11/1992 | Spies et al. | 73/146 |
| 5,510,272 A | * | 4/1996 | Morikawa et al. | 438/67 |
| 5,745,225 A | * | 4/1998 | Watanabe et al. | 356/4.01 |
| 5,815,272 A | * | 9/1998 | Harding | 356/623 |
| 5,864,145 A | * | 1/1999 | Krimermann et al. | 250/559.29 |
| 6,452,684 B1 | * | 9/2002 | Mennink | 356/601 |
| 6,615,648 B1 | * | 9/2003 | Ferguson et al. | 73/146 |

FOREIGN PATENT DOCUMENTS

| CA | 1 020 918 | 11/1977 |
|---|---|---|
| CA | 1 259 834 | 9/1989 |
| CA | 2 315 188 A1 | 7/1999 |

OTHER PUBLICATIONS

Fugro, "Fugro Consultants", http://www.bre.fugro.com (see pdf document entitled "Fugro ADVantage ©," 2p.).

(Continued)

*Primary Examiner*—Anand Bhatnagar
*Assistant Examiner*—Jose M Torres
(74) *Attorney, Agent, or Firm*—Merchant & Gould P.C.

(57) ABSTRACT

There is provided a vision system and a method for scanning a traveling surface such a road to detect surface defects thereof such as cracks. The vision system, which is mountable on a vehicle, is provided with a linear imaging system for imaging successive adjacent transversal linear portions of the traveling surface as the vehicle advances. The vision system is also provided with laser line projecting means angularly projecting a laser line onto the transversal linear portion of the traveling surface to be imaged in a substantially coplanar relationship with the linear imaging system. The present vision system is particularly devised to be immune to surrounding light conditions variations to provide optimum cracks image contrast for both transverse and longitudinal cracks.

15 Claims, 6 Drawing Sheets

OTHER PUBLICATIONS

Pathway Services Inc., "Automated Road and Pavement Condition Data Collection Systems," http://www.pathwayservices.com.

International Cybernetics Corporation, "Manufacturers of Custom Built Non-Destructive Pavement Test Equipment", http://www.intlcybernetics.com.

Roadware Group Inc., "The Source for Infrastructure Information", http://www.roadware.com.

Waylink Systems Corporation, "Tomorrow's Technology . . . ", http://www.waylink.com.

Fugro, "Fugro Consultants", http://www.bre.fugro.com (see pdf document entitled "Fugro ADVantage ©," 2p.), 2005.

Pathway Services Inc., "Automated Road and Pavement Condition Data Collection Systems," http://www.pathwayservices.com, 2004.

International Cybernetics Corporation, "Manufacturers of Custom Built Non-Destructive Pavement Test Equipment", http://www.intlcybernetics.com, 2005.

Roadware Group Inc., "The Source for Infrastructure Information", http://www.roadware.com, 2005.

Waylink Systems Corporation, "Tomorrow's Technology . . . ", http://www.waylink.com, 2005.

* cited by examiner

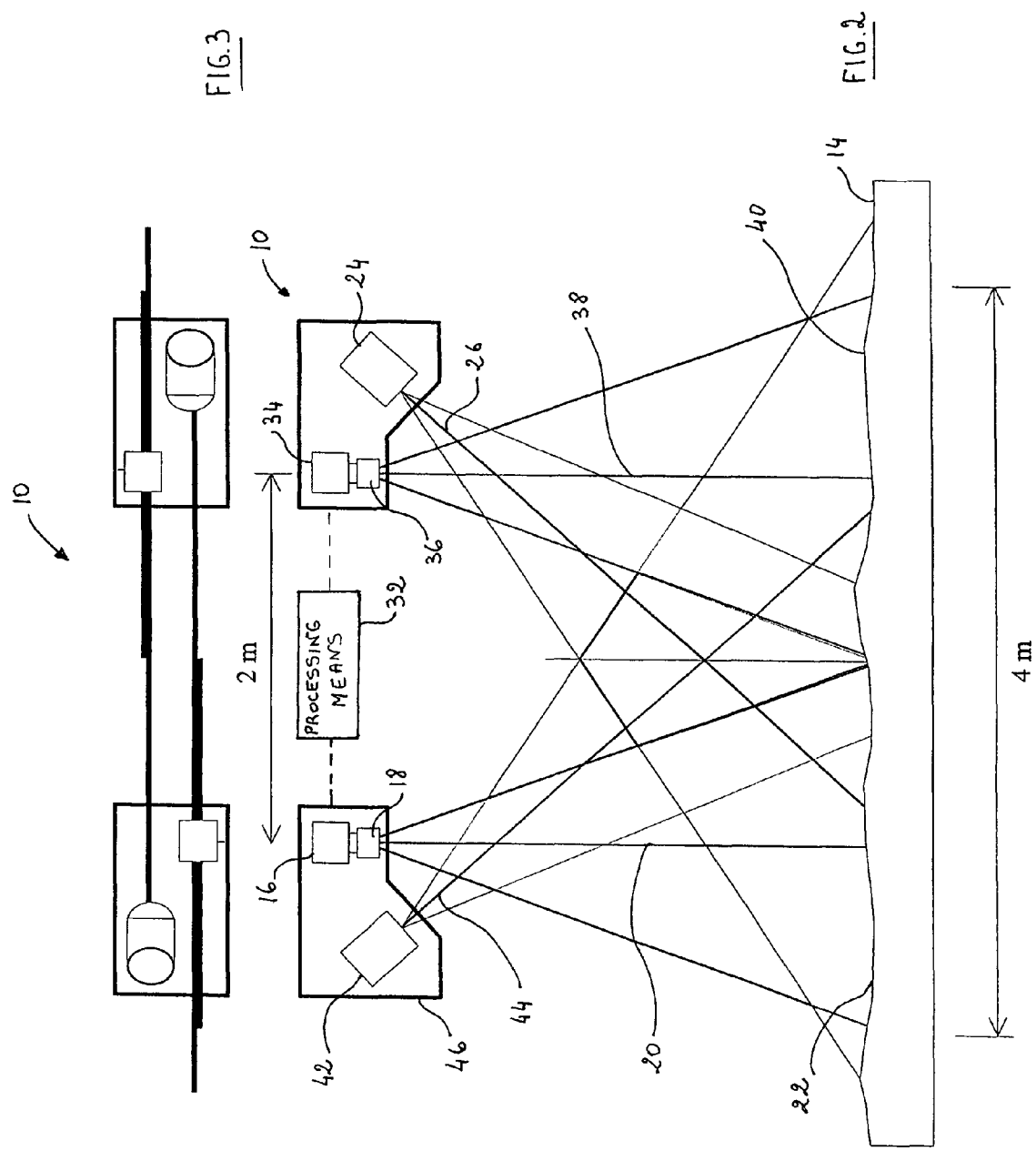

VISION SYSTEM AND A METHOD FOR SCANNING A TRAVELING SURFACE TO DETECT SURFACE DEFECTS THEREOF

FIELD OF THE INVENTION

The present invention generally relates to road visual inspection, and more particularly concerns a vision system and a method for scanning a traveling surface such as a road to detect surface defects thereof.

BACKGROUND OF THE INVENTION

Traveling surfaces such as roads, carriageways and the like are inherently subject to heavy wear from traffic and degradation from weather conditions and ground movements. It is known that wear of the roads foundations typically begins with the cracking of the pavement. This necessitates regular monitoring of the pavement condition to plan maintenance programs.

Fundamental to an effective maintenance and reconstruction program is the acquisition of accurate information concerning the condition of the pavement. At the present such procedures for obtaining this information are very time consuming and labor intensive and are inherently inaccurate and unreliable.

Despite a number of attempts that have been made to develop equipment for testing the condition of the pavement, most public agencies utilize a subjective system of analyzing the condition of the pavement by the human eye by directly viewing the pavement surface or indirectly viewing the pavement through the use of photographs and video that have been taken of the pavement. In the latter process, most often, the photos are analyzed by the human eye to determine the presence and severity of pavement distress features.

In a somewhat similar context, mobile equipment has been devised in the past for determining the roughness of the road or pavement. Indeed, vision systems mountable on a vehicle traveling onto a traveling surface such a road have been developed. However, most existing imaging systems, which use 2D cameras, often suffer from non-uniform lighting and shadows generally caused by the presence of the sun, trees, viaducts, buildings, the inspection vehicle itself or other vehicles as non-limitative examples. With these systems, detection of cracks is neither accurate nor reliable due to the limited resolution of the cameras and the poor contrast of the gathered images. Moreover, because of the presence of the sun, it is challenging task to maintain image quality under this highly variable and uncontrolled light.

For example, known in the art, there is an automated road and pavement condition data collection system proposed by the company Pathway services Inc. which relies on the use of 4 cameras. Two cameras are mounted in front of the vehicle for providing a first set of images while the remaining two cameras are mounted in the back of the vehicle for providing a second set of images. With this particular arrangement, generally, at least one of the two sets of images will not have shadows caused by the inspection vehicle. However, both sets of images may suffer from other shadows coming from surrounding trees, buildings for example. Moreover, this system is quite cumbersome since it relies on the use of a set of camera both in front and rear of the vehicle.

Also known in the art, there is a road inspection system proposed by Fugro-bre Inc. which relies on the use of a digital camera and synchronized strobe lights for inspecting the road. This system is mounted on the rear of a vehicle and is quite cumbersome. Moreover, this system has to operate at night-time to avoid shadows and difficult illumination conditions caused by the sun.

Also known in the art, there is the crack detection system developed by Roadware which uses matrix cameras with strobe lights to allow the system to operate in daytime. The cameras are capable of recording images at speeds up to 50 mph. One major disadvantage of such a configuration is that the angle between the strobe lights and the cameras are a cause a major non-uniformities in the images. This is caused by the fact that the pavement areas that are closer to the strobe lights appear much brighter than those further away, a lighting gradiant is thus created and reduces the quality of the images and contrasts.

Another system known in the art is the road inspection system that was proposed by both Waylink Corporation and International Cybernetics Corporation. Both these systems are provided with a single linescan camera which has to be extended high above the vehicle on which the system is mounted. The system is also provided with a large number of light bulbs in an attempt to produce a powerful uniform light line on the road to be inspected. The major disadvantage of this system is the large quantity of electricity needed, thousands of watts, to power the system. A generator is thus necessary to power the whole system. The whole system is thus cumbersome, and, moreover, it is not able to provide good shadow contrast in the images especially as pertains to longitudinal cracks.

None of the above mentioned inspection systems is adapted to perform a fast enough automatic accurate road inspection immune to surrounding light condition changes while providing a compact and power efficient assembly.

Therefore, it would be desirable to provide a vision system for scanning a traveling surface such as a road to detect surface defects thereof, and which would give optimum crack image contrasts for both transverse and longitudinal cracks, which would be immune to surrounding light condition variations, while being automatic, fast enough, compact and power efficient.

SUMMARY OF THE INVENTION

An object of the present invention is to provide a vision system for scanning a traveling surface to detect surface defects thereof that satisfies the above mentioned needs.

Accordingly, the present invention provides a vision system mountable on a vehicle traveling onto a traveling surface for scanning the traveling surface to detect surface defects thereof. The vision system is provided with a linear imaging system having a linear sensor directed towards the traveling surface substantially transversally thereto along an optical axis substantially perpendicular to the traveling surface for successively imaging adjacent transversal linear portions of the traveling surface as the vehicle advances, thereby providing corresponding adjacent transversal linear images of the traveling surface. The vision system is also provided with laser line projecting means extending distal from the imaging system. The laser line projecting means have a laser beam axis angularly directed towards the traveling surface in a substantially coplanar relationship with the optical axis and the linear sensor of the imaging system for angularly projecting a laser line along the laser beam axis across the traveling surface on the corresponding transversal portion thereof to generate a transverse profile thereof in the corresponding image. The vision system is also provided with processing means operatively connected to the imaging system for processing the adjacent transversal linear images, thereby allowing to detect surface defects on the traveling surface.

In a further embodiment of the invention, the vision system is further provided with an additional linear imaging system mountable on the vehicle distal from the imaging system. The additional linear imaging system has a linear sensor directed towards the traveling surface substantially transversally thereto along an optical axis substantially perpendicular to the traveling surface for successively imaging additional adjacent transversal linear portions of the traveling surface, each being transversally adjoined to a corresponding one of the transversal linear portions, thereby providing corresponding additional adjacent transversal linear images of the traveling surface. The vision system further has additional laser line projecting means mountable on the vehicle distal from the additional linear imaging system. The additional laser line projecting means have a laser beam axis angularly directed towards the traveling surface in a substantially coplanar relationship with the optical axis and the linear sensor of the additional imaging system for angularly projecting an additional laser line along the laser beam axis across the traveling surface on the corresponding additional transversal linear portion thereof to generate a transverse profile thereof in the corresponding additional image.

According to another aspect of the invention, there is also provided a vision method for scanning a surface to detect surface defects thereof. The vision method comprises the steps of:
a) providing a vehicle traveling on the surface, the vehicle being provided with a vision system comprising laser line projecting means for projecting a laser line on the surface and linear imaging means distal from the laser projecting means for imaging the laser line;
b) angularly projecting the laser line across the surface within a laser projection plane extending in a substantially transversal and perpendicular relationship with the surface;
c) successively imaging the laser line substantially perpendicularly to the surface in a substantially coplanar relationship with the laser projection plane for providing successive adjacent transversal linear images of the surface as the vehicle advances; and
d) processing the adjacent transversal linear images for detecting surface defects on the surface.

In a further preferred embodiment of this method, the step b) further comprises the sub-step of angularly projecting an additional laser line across the surface within a distinct additional laser projection plane adjoining the laser projection plane and extending in a substantially transversal and perpendicular relationship with the surface. The step c) further comprises the sub-step of successively imaging the additional laser line substantially perpendicularly to the surface in a substantially coplanar relationship with the additional laser projection plane.

BRIEF DESCRIPTION OF THE DRAWINGS

These and other objects and advantages of the invention will become apparent upon reading the detailed description and upon referring to the drawings in which:

FIG. 2 is a schematic representation of another vision system according to the present invention.

FIG. 3 is a top view of the vision system shown in FIG. 2.

Figure 1:
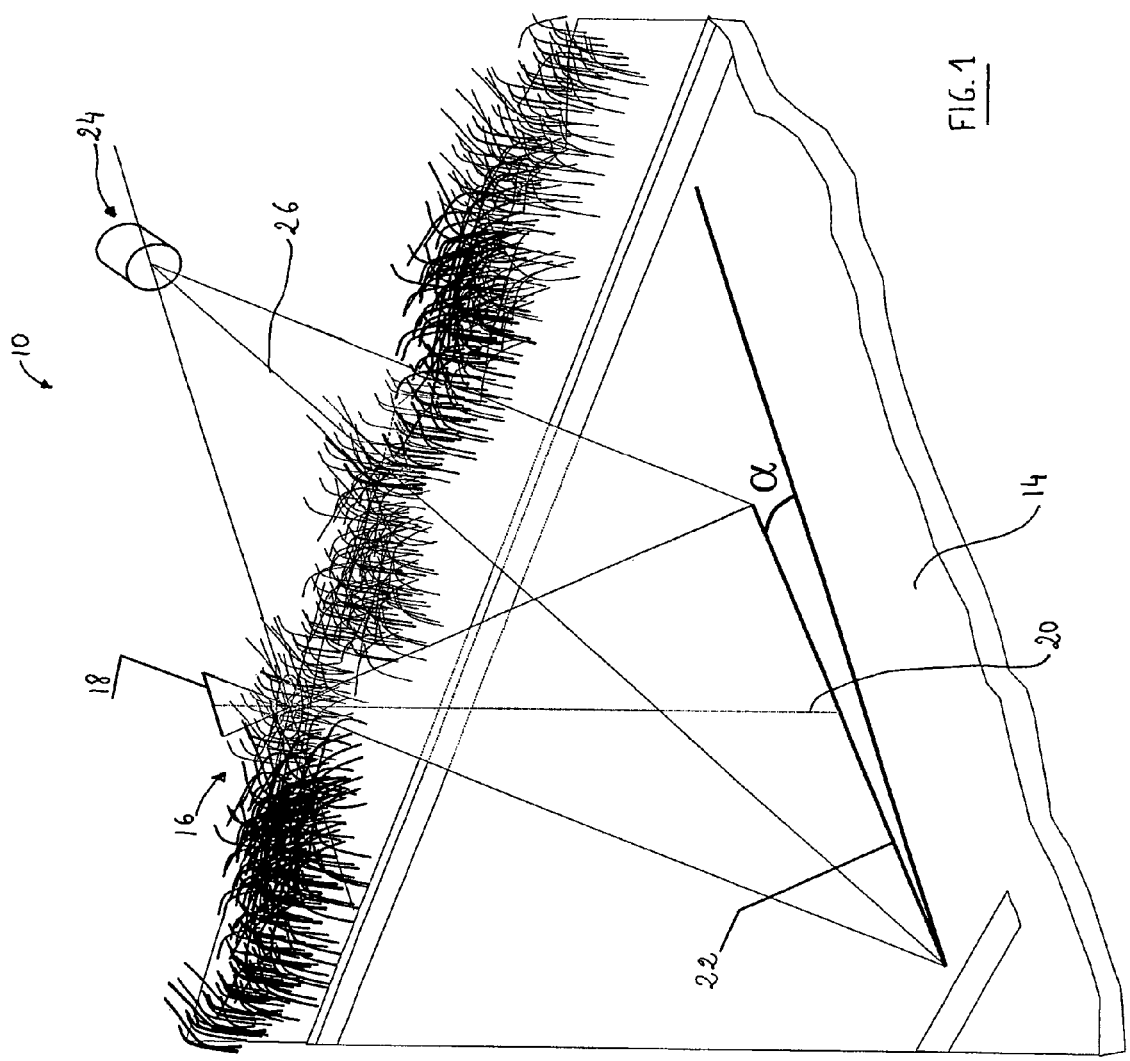
FIG. 1 is a perspective schematic representation of a vision system according to the present invention.

While the invention will be described in conjunction with example embodiments, it will be understood that it is not intended to limit the scope of the invention to such embodiments. On the contrary, it is intended to cover all alternatives, modifications and equivalents as may be included as defined by the appended claims.

DESCRIPTION OF PREFERRED EMBODIMENTS

In the following description, similar features in the drawings have been given similar reference numerals and, in order to weight down the figures, some elements are not referred to in some figures if they were already identified in a precedent figure.

The present invention concerns a vision system which is mountable on a vehicle, such a van or a trailor for example, traveling onto a traveling surface such a road as a non-limitative example for scanning the traveling surface to detect surface defects thereof. The vision system, which can also be referred to as a pavement inspection apparatus, is capable of providing very reliable and accurate information on the road conditions, specially concerning the longitudinal and transversal profile of the pavement. Indeed, the vision system of the present invention is particularly devised to be immune to surrounding light condition variations, thereby allowing to provide optimum cracks image contrast for both transverse and longitudinal cracks.

In a particularly advantageous embodiment which will be described in details thereinafter with reference to FIGS. 2 and 3, the vision system can advantageously perform the inspection of a full lane width of pavement, such as 4 meter width. Moreover, the inspection task can advantageously be performed during normal traffic hours with the vehicle moving at normal traffic speed such as 100 km per hour without requiring the use of any special traffic procedures nor disrupting, detouring or slowing normal traffic.

Moreover, the present vision system uses laser light for illuminating the traveling surface, contrary to the prior art devices which use conventional lighting requiring a lot of energy. Thus, the vision system proposed by the present invention has the great advantage of being very power efficient in comparison to the existing devices, while being capable of operating during night or day.

Referring now to FIG. 1 there is shown a vision system 10 according to the present invention. The vision system 10 is devised to be mountable on a vehicle 12, as better shown in FIG. 4. Preferably, the vision system 10 is mounted on the rear of the vehicle 12 which is able to travel onto a traveling surface 14, such as a road, for scanning the traveling surface 14 to detect surface defects thereof. It is worth mentioning that the vision system of the present invention could also be used to scan any convenient substantially plane surface in relative motion with respect to the vision system, but is nevertheless particularly intended to scan traveling surfaces such as roads, or even sidewalks and could also be easily adapted to scan a railway as a non-limitative example. The vision system 10 is provided with a linear imaging system 16 having a linear sensor 18 directed towards the traveling surface 14 substantially transversally thereto along an optical axis 20 substantially perpendicular to the traveling surface 14. The linear imaging system 16 is thus able to image any forms or objects located in the plane extending along the optical axis 20 in alignment relationship with the linear sensor 18. The linear imaging system 16 is thus able to successively image adjacent transversal linear portions 22 of the traveling surface 14 as the vehicle 12 advances, thereby providing corresponding adjacent transversal linear images of the traveling surface 14. As illustrated in FIG. 1, by the expression "substantially transversally", it is meant that the linear sensor 18 can image a linear portion 22 of the surface 14 extending in a transversal manner across the traveling surface 14. Of course the imaged linear portion 22 can be really transversal to the traveling surface 14 but can also advantageously extend at a slant scanning angle α, preferably comprised between 0 and 45 degrees. In a more preferred embodiment and as illustrated in FIG. 1, the slant scanning angle is rather quite small, preferably 5 degrees. This particular arrangement, in combination with the lighting system which will be described thereinafter, advantageously provides linear images wherein both transversal and longitudinal cracks of the road are more easily enhanced.

The vision system 10 is also provided with laser line projecting means 24 extending distal from the imaging system 16. The laser line projecting means, such a laser projector for example, has a laser beam axis 26 angularly directed towards the traveling surface 14 in a substantially coplanar relationship with the optical axis 20 and the linear sensor 18 of the imaging system 16. This allows to angularly projecting a laser line along the laser beam axis 26 across the traveling surface 14 on the corresponding transversal portion 22 thereof to generate a transverse profile thereof in the corresponding image. Preferably, the laser line projecting means 24 is provided with a high power laser. This allows to use the vision system during the day, either in sunny regions or shady regions, or even a mix of the both, without being negatively affected by shadows nor surrounding lighting conditions variations. In fact, the linear imaging system 16 is advantageously further provided with an optical filter (not shown) extending in front of the linear sensor 18 and particularly chosen to filter sun light while transmitting the laser light. This specific embodiment is particularly advantageous since it renders the present system immune to surrounding light condition changes, thereby providing a reliable and repeatable detection of surface defects.

Moreover, the specific arrangement of the laser line projecting means 24 which is particularly angularly positioned with respect to the imaging system 16 advantageously provides an enhancement of the apparent contrast of the cracks. Indeed, as explained above, the laser beam axis 26 of the laser line projecting means 24, the laser line, the optical axis 20 of the linear sensor 18 and the linear sensor 18 itself, all extend in a coplanar relationship with each other. This coplanar relationship advantageously provides a great depth of view of the sensor 18. Thus, the road portion to be imaged is always illuminated whatever the distance between the laser line projecting means 24 and the road. In fact, without this particular relationship, the laser line and the portion of the road seen by the linear sensor 18 will overlap only for a predetermined distance between the road and the vision system itself. Since the vehicle traveling on the road to be inspected is subject to up and down movements which continuously vary the distance between the laser line projecting means 24 and the road, the vision system 10 has to have a sufficiently good depth of field.

Figure 6:
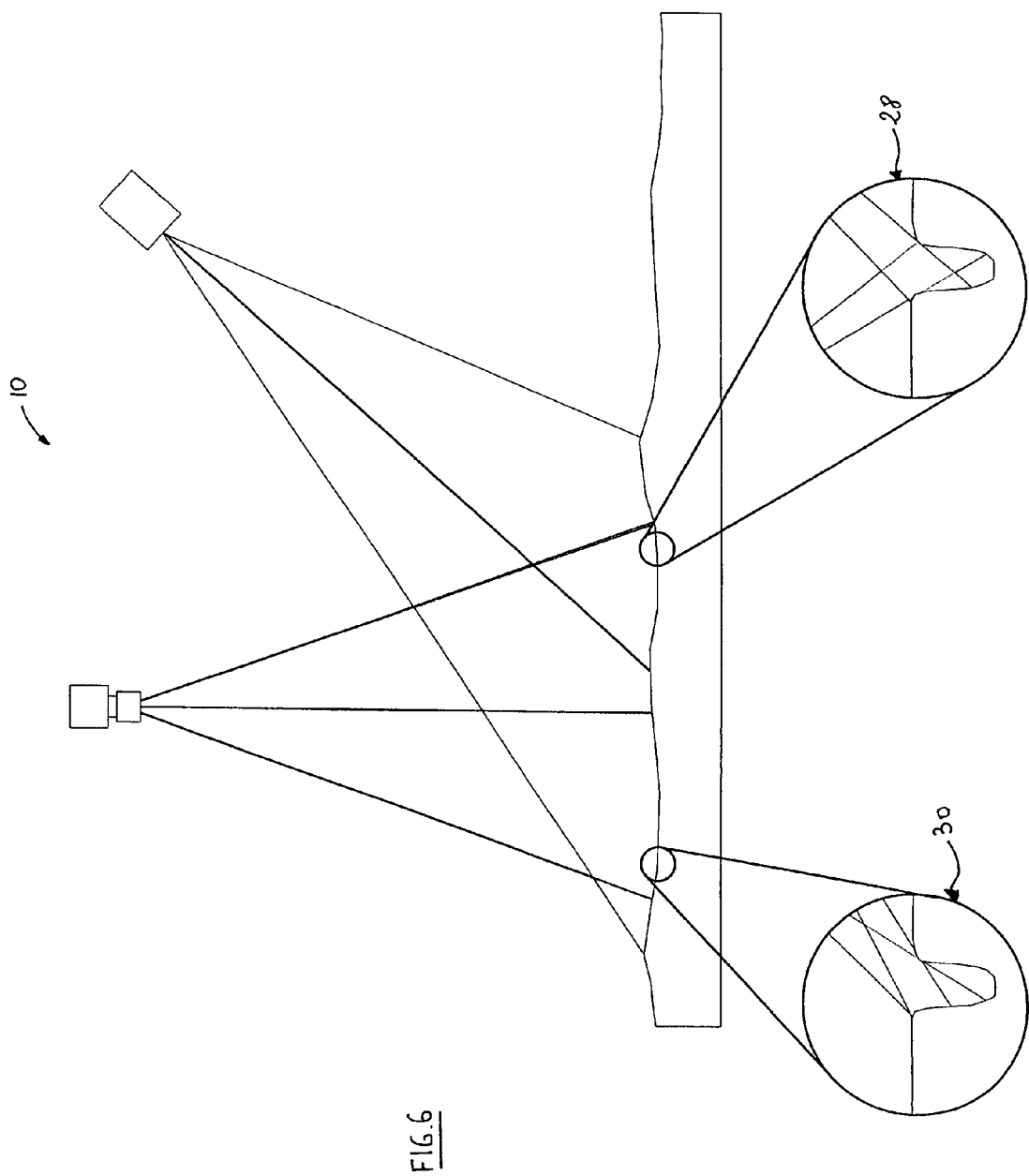
FIG. 6 is another schematic representation of the vision system shown in FIG. 1.

With reference now to FIG. 6, there is illustrated the shadow effects generated by the angular laser light projection. This particular arrangement advantageously allows an enhancement of the visibility of the cracks of the road. In the road crack 28 in the right of FIG. 6, the sensor 18 only sees the right side of the crack while the laser line only illuminates its left side. In the road crack 30 in the left of the FIG. 6, the sensor 18 sees the left side of the crack which is only partly illuminated by the laser line because of the more strongly marked incidence angle of the laser line.

Figure 8:
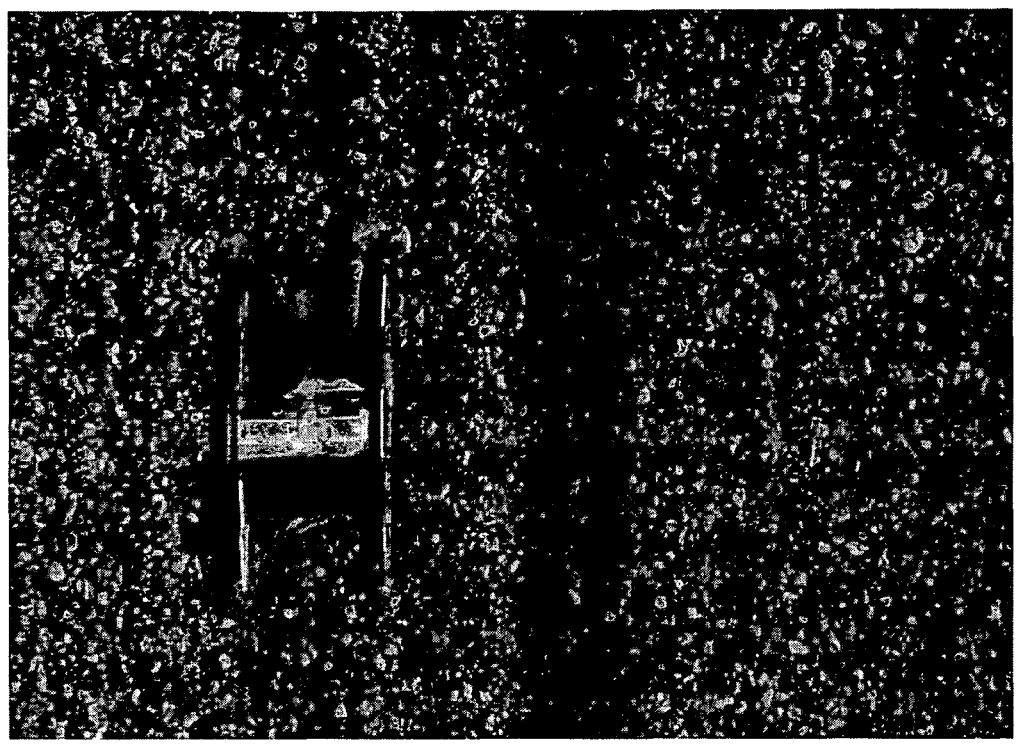
FIG. 8 shows a road portion imaged with the vision system of the present invention.
Figure 9:
FIG. 9 shows another road portion imaged with the system of the present invention.

FIGS. 8 and 9 illustrate two distinct portions of a road which have been imaged, at 100 km/h with the present vision system 10. One can clearly see that both longitudinal and transversal cracks are well enhanced and are thus easily detectable. Indeed, in the preferred embodiment of the present invention, the linear sensor is advantageously a linear 2048 pixels camera providing a precise detection of cracks as low as 1 millimetre width. Even the texture of the road can be seen. FIG. 8, which shows a portion of a road provided with a tag, well illustrates the resolution that can be reached with the present system.

Referring now to FIG. 2, which shows another preferred embodiment of the present invention which will be described in more details thereinafter, the vision system 10 is also provided with processing means 32, such a computer, which is operatively connected to the imaging system 16 for processing the adjacent transversal linear images, thereby allowing to detect surface defects on the traveling surface 14. With the expression "processing the adjacent transversal linear images", it is to be understood that the processing means is able to record the images for an immediate or subsequent inspection, which can be made by human eyes or automatically with an appropriate software. The processing means may also advantageously allow generation of reports and characterization of the surface defects. The processing means may also advantageously be provided with a global positioning system for performing a road mapping of the inspected roads and localization of defects thereof.

Figure 4:
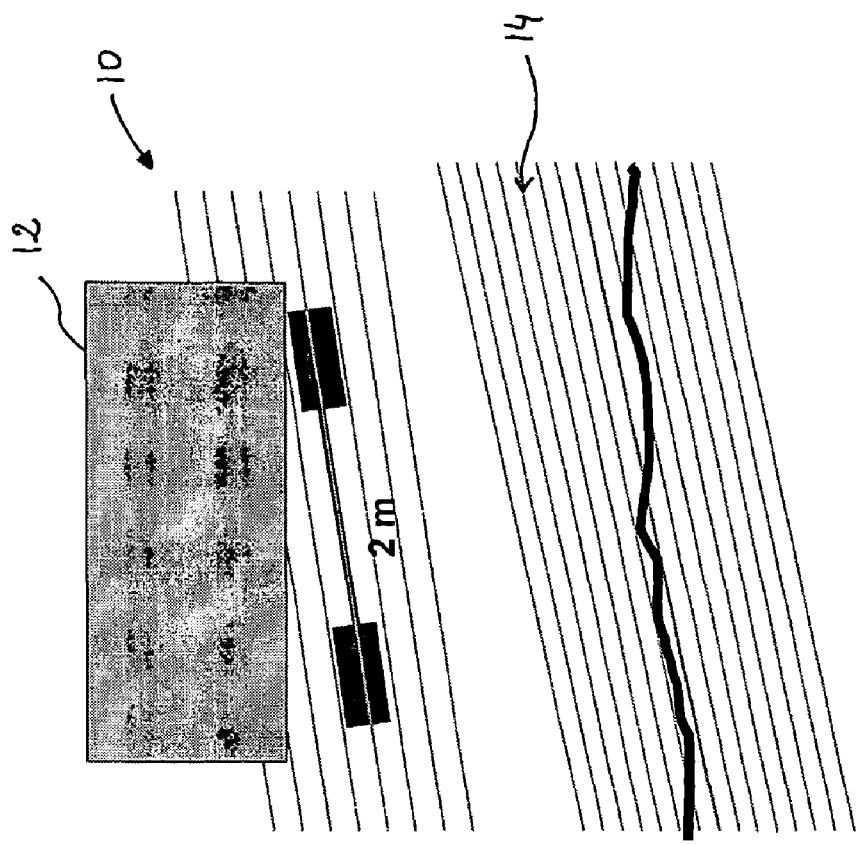
FIG. 4 is a schematic representation showing a vehicle onto which the vision system of FIG. 2 is mounted.
Figure 5:
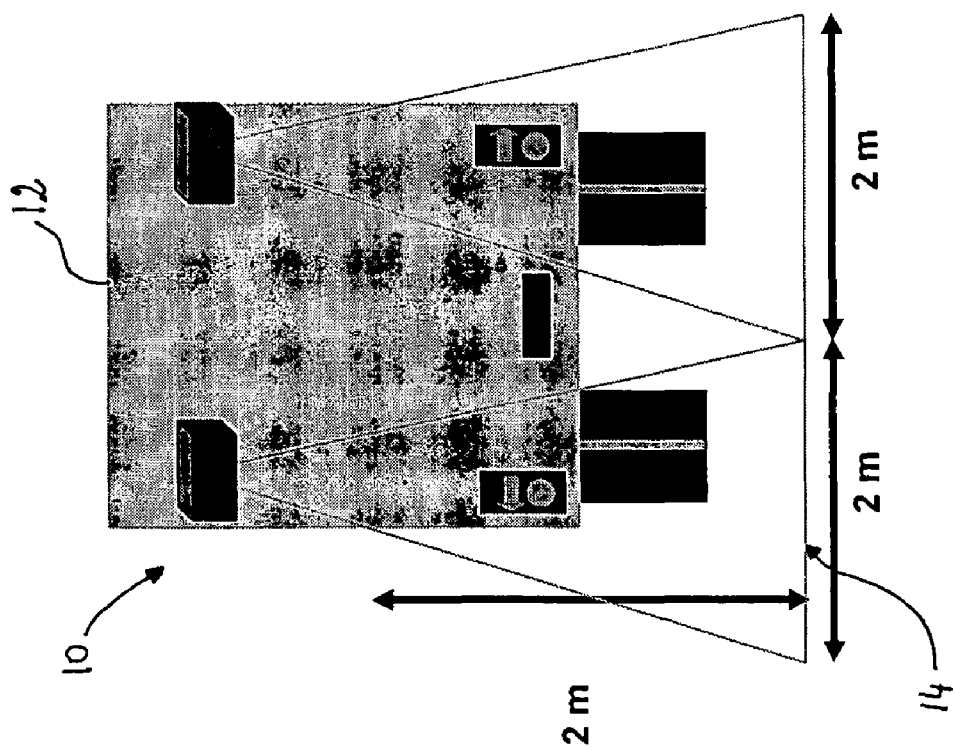
FIG. 5 is a top view of the vehicle shown in FIG. 4.

Referring now to FIGS. 3 to 5 and still to FIG. 2, there is shown a more preferred embodiment of the present vision system 10. In this preferred embodiment, the vision system 10 is advantageously provided with an additional linear imaging system 34 which is mountable on the vehicle 12 distal from the imaging system 16. The additional linear imaging system 34 has a linear sensor 36 directed towards the traveling surface 14 substantially transversally thereto along an optical axis 38 substantially perpendicular to the traveling surface 14. This arrangement allows to successively imaging additional adjacent transversal linear portions 40 of the traveling surface 14, each being transversally adjoined to a corresponding one of the transversal linear portions 22, thereby providing corresponding additional adjacent transversal linear images of the traveling surface 14. As explained above with reference to FIG. 1, by the expression "substantially transversally", it is meant that the linear sensor 34 can image a linear portion 40 of the surface 14 extending in a transversal manner across the traveling surface 14. Of course the imaged linear portion 40 can be really transversal to the traveling surface 14 but can also advantageously extend at a slant scanning angle α, preferably comprised between 0 and 45 degrees. In a more preferred embodiment and as illustrated in FIG. 5, the slant scanning angle is rather quite small, preferably 5 degrees. The slant angle is used to advantageously increase the contrast of transverse cracks using the same principle as was described in FIG. 6 for the enhancement longitudinal cracks. In this preferred embodiment, the vision system 10 further has additional laser line projecting means 42 which are mountable on the vehicle 12 distal from the additional linear imaging system 34. The additional laser line projecting means 42 have a laser beam axis 44 angularly directed towards the traveling surface 14 in a substantially coplanar relationship with the optical axis 38 and the linear sensor 36 of the additional imaging system 34. This particular arrangement allows to angularly projecting an additional laser line along the laser beam axis 44 across the traveling surface 14 on the corresponding additional transversal linear portion 40 thereof to generate a transverse profile thereof in the corresponding additional image. This particular embodiment is very advantageous for performing inspection of a full lane width of pavement of 4 meter width for example. In a most preferred embodiment, each of the sensors 16, 34 comprises a 2048 pixels linear camera allowing to provide at least 28000 profiles per second. This provides a lateral resolution of 1 mm and a longitudinal resolution of 1 mm when the vehicle travels at 100 km per hour.

Preferably, with reference to FIG. 3, each of the laser line and additional laser line extends on the traveling surface 14 in a parallel relationship with each other. Also preferably, each of the laser line and additional laser line extends on the traveling surface 14 in a non-collinear relationship with each other. Still preferably, each of the laser line and additional laser line extends on the traveling surface 14 in a non-overlapping relationship in order to prevent potential saturation of the sensors 18, 36 which could eventually result.

Still referring to FIGS. 2 to 5, in this illustrated preferred embodiment, the laser line projecting means 24 advantageously extend proximal to the additional imaging system 34. The additional laser line projecting means 42 advantageously extend proximal to the imaging system 16. This particular arrangement allows to projecting the corresponding laser lines on the traveling surface 14 in a non-overlapping cross configuration. Preferably, each of the laser line projecting means 24, 42 extend outwards to the corresponding one of the imaging systems 16, 34, but it could also be contemplated to mount each of the projecting means 24, 42 between the two imaging systems 16, 34.

Figure 7:
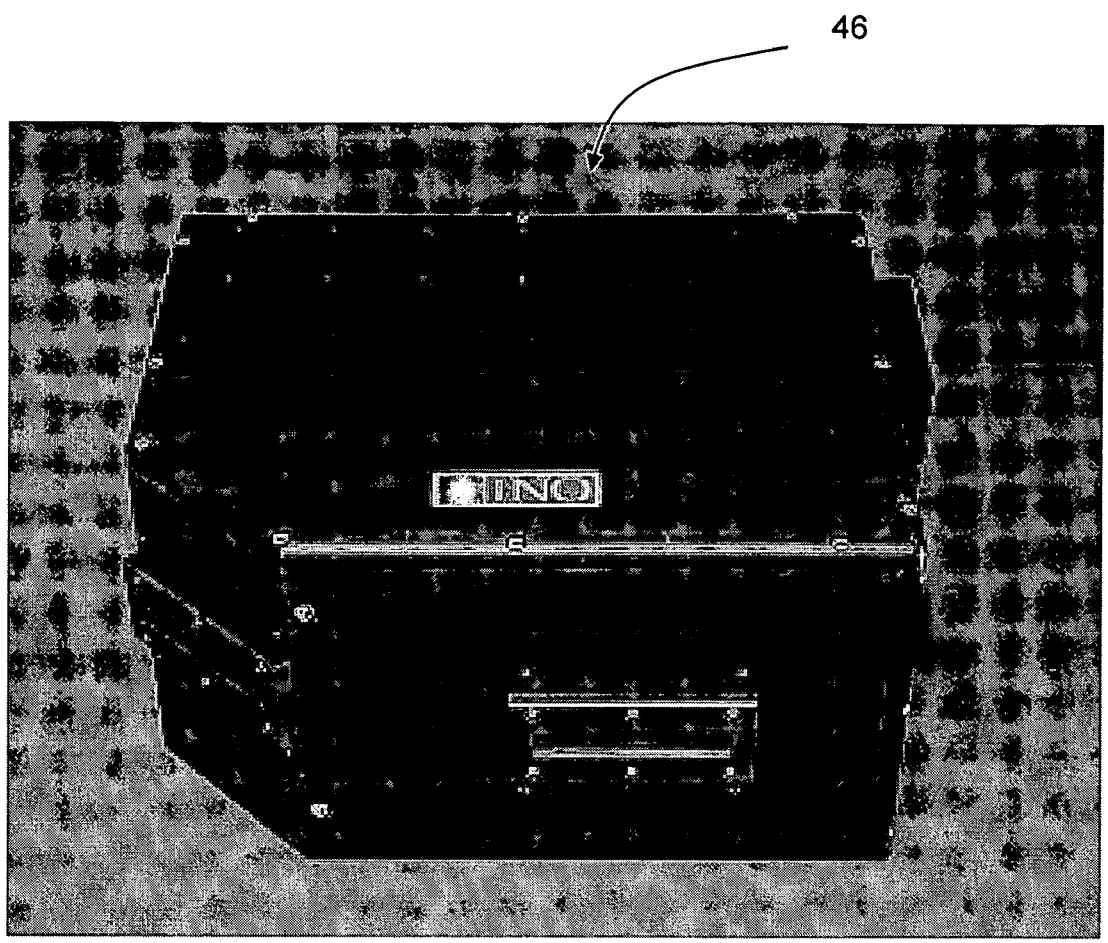
FIG. 7 shows a perspective view of a casing of the vision system of the present invention.

Still referring to FIGS. 2 to 5 and also to FIG. 7, in a further preferred embodiment, the vision system of the present invention may advantageously be provided with a first and a second casing 46, 48, each being mountable on the vehicle 12. The first casing 46 receives the imaging system 16 and the additional laser projecting means 42 while the second casing 48 receives the additional imaging system 34 and the laser projecting means 24 therein. In other words, the right hand projecting means illuminate a portion of the road seen by the left hand camera and vice versa. Connecting and supporting the casings 46, 48 is advantageously a high torsion resistant beam (not illustrated) that provides a heavy rigidity to the whole system 10 in order to prevent misalignments between the projected laser lines and the imaged road portions 22, 40, while providing a compact assembly. As particularly illustrated in FIG. 5, in this preferred embodiment, each of the laser line and additional laser line advantageously extends substantially transversally on the traveling surface in a parallel relationship to each other at a slant scanning angle comprised between 0 and 45 degrees, and more preferably at a slant scanning angle of 5 degrees. Preferably, as better shown in FIG. 2, each of the laser lines extends in a non collinear relationship to each other, as previously mentioned.

According to another aspect, the present invention also provides a vision method for scanning a surface to detect surface defects thereof. The vision method comprises the steps of:

a) providing a vehicle traveling on the surface, the vehicle being provided with a vision system comprising laser line projecting means for projecting a laser line on the surface and linear imaging means distal from the laser projecting means for imaging the laser line;
b) angularly projecting the laser line across the surface within a laser projection plane extending in a substantially transversal and perpendicular relationship with the surface;
c) successively imaging the laser line substantially perpendicularly to the surface in a substantially coplanar relationship with the laser projection plane for providing successive adjacent transversal linear images of the surface as the vehicle advances; and
d) processing the adjacent transversal linear images for detecting surface defects on the surface.

Referring again to FIGS. 4 and 5, in a further preferred embodiment of this method, the step b) further comprises the sub-step of angularly projecting an additional laser line across the surface within a distinct additional laser projection plane adjoining the laser projection plane and extending in a substantially transversal and perpendicular relationship with the surface. The step c) further comprises the sub-step of successively imaging the additional laser line substantially perpendicularly to the surface in a substantially coplanar relationship with the additional laser projection plane.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

What is claimed is:

1. A vision system mountable on a vehicle traveling onto a traveling surface for scanning said traveling surface to detect surface defects thereof, said vision system comprising:

a linear imaging system having a linear sensor directed towards said traveling surface substantially transversally thereto for successively imaging adjacent transversal linear portions of said traveling surface as said vehicle advances, the linear imaging system providing corresponding adjacent transversal linear images of said traveling surface;

laser line projecting means having a laser beam axis angularly directed towards said traveling surface for angularly projecting a laser line along said laser beam axis across said traveling surface to generate a transverse profile thereof in the corresponding image; said linear imaging system and said laser line projecting means lying in a same plane, said plane being substantially perpendicular to said traveling surface and transverse to said traveling surface; and processing means operatively connected to said imaging system for processing said adjacent transversal linear images, thereby detecting surface defects on said traveling surface; wherein said vision system comprises an additional linear imaging system mountable on said vehicle distal from said imaging system, said additional linear imaging system having a linear sensor directed towards said traveling surface substantially transversally thereto along an optical axis substantially perpendicular to said traveling surface for successively imaging additional adjacent transversal linear portions of said traveling surface, each being transversally adjoined to a corresponding one of said transversal linear portions, thereby providing corresponding additional adjacent transversal linear images of said traveling surface, said vision system further comprising additional laser line projecting means mountable on said vehicle distal from said additional linear imaging system and having a laser beam axis angularly directed towards said traveling surface in a substantially coplanar relationship with the optical axis and the linear sensor of said additional imaging system for angularly projecting an additional laser line along said laser beam axis across said traveling surface on the corresponding additional transversal linear portion thereof to generate a transverse profile thereof in the corresponding additional image.

2. The vision system according to claim 1, wherein said laser line extends substantially transversally on said traveling surface at a slant scanning angle comprised between 0 and 45 degrees.

3. The vision system according to claim 2, wherein said slant scanning angle is 5 degrees.

4. The vision system according to claim 1, wherein said linear imaging system is provided with an optical filter extending in front of the linear sensor.

5. The vision system according to claim 1, wherein each of said laser line and additional laser line extends on said traveling surface in a parallel relationship with each other.

6. The vision system according to claim 1, wherein each of said laser line and additional laser line extends on said traveling surface in a non-collinear relationship with each other.

7. The vision system according to claim 1, wherein each of said laser line and additional laser line extends on said traveling surface in a non-overlapping relationship.

8. The vision system according to claim 1, wherein each of said laser lines extends substantially transversally on said traveling surface in a substantially parallel relationship with each other at a slant scanning angle comprised between 0 and 45 degrees.

9. The vision system according to claim 8, wherein said slant scanning angle is 5 degrees.

10. The vision system according to claim 1, wherein said laser line projecting means extend proximal to said additional imaging system and said additional laser line projecting means extend proximal to said imaging system for projecting the corresponding laser lines on said traveling surface in a non-overlapping cross configuration.

11. The vision system according to claim 10, wherein each of said laser line projecting means extends outwards to the corresponding one of said imaging systems.

12. The vision system according to claim 10 wherein each of said laser line projecting means projects the corresponding laser line on said traveling surface in a parallel and non-collinear relationship to each other.

13. The vision system according to claim 10, wherein said vision system further comprises a first and a second casing, each being mountable on said vehicle, said first casing receiving said imaging system and said additional laser projecting means while said second casing receives said additional imaging system and said laser projecting means therein.

14. The vision system according to claim 13, wherein each of said laser line and additional laser line extends substantially transversally on said traveling surface in a parallel and non-collinear relationship to each other at a slant scanning angle of 5 degrees.

15. A method for scanning a surface to detect surface defects thereof, said method comprising the steps of:
 a) providing a vehicle traveling on said surface, said vehicle being provided with a vision system comprising laser line projecting means for projecting a laser line on said surface and linear imaging means distal from said laser projecting means for imaging said laser line said laser line projecting means and said linear imaging means lying in a same plane;
 b) i) angularly projecting said laser line across said surface within a laser projection plane extending in a substantially transversal and perpendicular relationship with said surface; and
  ii) angularly projecting an additional laser line across said surface within a distinct additional laser projection plane adjoining said laser projection plane and extending in a substantially transversal and perpendicular relationship with said surface:
 c) i) successively imaging said laser line substantially perpendicularly to said surface in a substantially coplanar relationship with said laser projection plane for providing successive adjacent transversal linear images of said surface as said vehicle advances; and
  ii) successively imaging said additional laser line substantially perpendicularly to said surface in a substantially coplanar relationship with said additional laser projection plane; and
 d) processing with a computer said adjacent transversal linear images for detecting surface defects on said surface.

* * * * *